(12) United States Patent
Ray et al.

(10) Patent No.: US 7,833,987 B2
(45) Date of Patent: Nov. 16, 2010

(54) SMALL SYNTHETIC RNA, A METHOD OF PREPARING THE SAME AND USES THEREOF

(75) Inventors: Partho Sarothi Ray, Bangalore (IN); Saumitra Das, Bangalore (IN)

(73) Assignee: Indian Institute of Science, Bangalore, IN (US)

( * ) Notice: Subject to any disclaimer, the term of this patent is extended or adjusted under 35 U.S.C. 154(b) by 133 days.

(21) Appl. No.: 10/598,700

(22) PCT Filed: Mar. 10, 2005

(86) PCT No.: PCT/IN2005/000078

§ 371 (c)(1), (2), (4) Date: Sep. 8, 2006

(87) PCT Pub. No.: WO2005/087923

PCT Pub. Date: Sep. 22, 2005

(65) Prior Publication Data

US 2008/0015159 A1    Jan. 17, 2008

(30) Foreign Application Priority Data

Mar. 12, 2004    (IN)    .......................... 224/CHE/2004

(51) Int. Cl.
*A61K 31/70*    (2006.01)
*C07H 21/02*    (2006.01)
*C07H 21/04*    (2006.01)
*C12Q 1/68*    (2006.01)

(52) U.S. Cl. .................... 514/44 R; 536/23.1; 536/24.1; 536/24.5; 435/6; 435/375; 435/455; 435/320.1; 435/91.1; 435/91.3; 435/91.32

(58) Field of Classification Search ....................... None
See application file for complete search history.

(56) References Cited

U.S. PATENT DOCUMENTS 6,127,116 A * 10/2000 Rice et al. .................... 435/6

FOREIGN PATENT DOCUMENTS

WO    WO 94/05813 A1    3/1994
WO    WO 03/087138 A2    10/2003

OTHER PUBLICATIONS

Ray et al. NAR vol. 32(5):1678-87, Mar. 12, 2004.*
Imbert, I., et al., "Hepatitis C virus IRES efficiency is unaffected by the genomic RNA 3'NTR even in the presence of viral structural or non-structural proteins" *Journal of General Virology*, 2003, vol. 84, pp. 1549-1557.
Tallet-Lopez, B., et al. "Antisense oligonucleotides targeted to the domain IIId of the hepatitis C virus IRES compete with 40S ribosomal subunit binding and prevent in vitro translation" *Nucleic Acids Research*, 2003, vol. 31, No. 2, pp. 734-742.

* cited by examiner

*Primary Examiner*—Sean R McGarry
(74) *Attorney, Agent, or Firm*—Lathrop & Gage LLP (57) ABSTRACT

Translation of the hepatitis C virus (HCV) RNA is mediated by the interaction of ribosomes and cellular proteins with an internal ribosome entry site (IRES) located within the 5'untranslated region (5'UTR). We have investigated whether small RNA molecules corresponding to the different stem-loop (SL) domains of the HCV IRES, when introduced in trans, can bind to the cellular proteins and antagonize their binding to the viral IRES, thereby inhibiting HCV IRES-mediated translation. We have found that an RNA molecule corresponding to SL III of the HCV IRES could efficiently inhibit HCV IRES-mediated translation in a dose-dependent manner without affecting cap-dependent translation. The SL III RNA was also found to bind efficiently to most of the cellular proteins which interacted with the HCV 5'UTR. A smaller RNA corresponding to SL e+f of domain III also strongly and selectively inhibited HCV IRES-mediated translation. This RNA molecule showed strong interaction with the ribosomal S5 protein and prevented the recruitment of the 40S ribosomal subunit by the HCV IRES. In conclusion our results demonstrate a novel approach to selectively block HCV RNA translation using a small RNA molecules mimicking the structure of the stem-loop IIIe+f subdomain of the HCV-IRES. The discovery provides a basis for developing a potent antiviral therapy targeting the interaction between the ribosome and the HCV-IRES RNA.

13 Claims, 9 Drawing Sheets

Fig.1: Dose-dependent inhibition of HCV IRES-mediated translation *in vitro* by SL III RNA Fig. 2: Effect of SL III RNA on HCV IRES-mediated translation *in vivo*

Figure 3: Constitutive expression of SL III RNA does not cause general inhibition of cellular transcriprtion and trauslation.

Figure 4: Specific inhibition of HCV IRES-mediated translation *in vitro* by SL III e+f RNA Figure 5: Effect of SL III e+f RNA on HCV IRES-mediated translation *in vivo*.

Figure 6: SL III e+f (A297G) RNA fails to bind to S5 ribosomal protein and does not inhibit HCV IRES-mediated translation.

Figure 7: SL III e+f prevents 40s ribosomal subunit recruitment by the HCV IRES

A

B

Figure 8: SL III e+f does not prevent ribosome recruitment by a capped RNA and binds directly to the 40S subunit.

Figure 9: Proposed model of inhibition of HCV IRES-mediated translation by SL III e+f RNA.

SEQUENCE LISTING

<160> NUMBER OF SEQ ID NOS: 5

<210> SEQ ID NO 1
<211> LENGTH: 62
<212> TYPE: DNA

```
<213> ORGANISM: Artificial
<220> FEATURE:
<223> OTHER INFORMATION: Synthetic oligonucleotide

<400> SEQUENCE: 1
gggagggccc tctcggtaga acaccatgac ggactatccc acgaacgctc acggggccct    60
cc                                                                   62

<210> SEQ ID NO 2
<211> LENGTH: 333
<212> TYPE: RNA
<213> ORGANISM: Hepatitis C virus

<400> SEQUENCE: 2
cuccccugug aggaacuacu gucuucacgc agaaagcguc uagccauggc guuaguauga    60
gugucgugca gccuccagga ccccccucc cgggagagcc auaguggucu gcggaaccgg    120
ugaguacacc ggaauugcca ggacgaccgg guccuuucuu ggauuaaccc gcucaaugcc    180
uggagauuug ggcgugcccc cgcgagacug cuagccgagu aguguugggu cgcgaaaggc    240
cuugugguac ugccugauag ggugcuugcg agugccccgg gaggucucgu agaccgugca    300
ucaugagcac gaauccuaaa ccucaaagaa aaa                                 333

<210> SEQ ID NO 3
<211> LENGTH: 199
<212> TYPE: RNA
<213> ORGANISM: Hepatitis C virus

<400> SEQUENCE: 3
ccucccggga gagccauagu ggucugcgga accggugagu acaccggaau ugccaggacg    60
accggguccu uucuuggauu aacccgcuca augccuggag auuugggcgu gccccgcga    120 gacugcuagc cgaguagugu gggucgcga aaggccuugu gguacugccu gauaggguc     180 uugcgagugc cccgggagg                                                 199

<210> SEQ ID NO 4
<211> LENGTH: 62
<212> TYPE: RNA
<213> ORGANISM: Hepatitis C virus

<400> SEQUENCE: 4
cccucccggg agagccaucu ugugguacug ccugauaggg ugcuugcgag ugccccggga    60
gg                                                                   62

<210> SEQ ID NO 5
<211> LENGTH: 62
<212> TYPE: RNA
<213> ORGANISM: Artificial
<220> FEATURE:
<223> OTHER INFORMATION: HCV SL III e+f subdomain with mutation A297G

<400> SEQUENCE: 5
cccucccggg agagccaucu ugugguacug ccugaugggg ugcuugcgag ugccccggga    60
gg                                                                   62
```

SMALL SYNTHETIC RNA, A METHOD OF PREPARING THE SAME AND USES THEREOF

This invention relates to a small synthetic ribonucleic acid (RNA) sequence and to method of preparing the same and use of the said sequence as a therapeutic molecule against hepatitis C induced liver cirrhosis and hepato cellular carcinoma.

PRIOR ART

HCV (Hepatitis C virus) is a major human pathogen with an estimated 170 million chronic carriers throughout the world, many of whom are at a significant risk for developing liver cirrhosis and hepatocellular carcinoma (1). Current therapeutic strategies using Interferon-α, either alone or in combination with ribavirin, have poor efficacy (2). Moreover, an important lesson obtained from the therapy of other viral infections is that multiple drug targets are required to prevent the emergence of drug-resistant varieties of the virus (3).

HCV is a positive stranded RNA virus and the translation of the viral genomic RNA is an early obligatory step of the infection process. The translation initiation of the uncapped viral RNA takes place through the IRES (internal ribosome entry site) located in the 5'UTR (5'-untranslated region) (4). Translation initiation from the IRES is mediated by a number of cellular trans-acting factors like the La autoantigen (5) and polypyrimidine tract-binding protein (PTB) (6) together with some canonical eIFs (eukaryotic Initiation Factors) like eIF3 (7), eIF2 and eIF2B (8). It has been suggested that the IRES acts as a structural scaffold with specifically placed recognition sites for recruiting the translation machinery (9). As this mechanism of translation initiation is distinct from the cellular cap-dependent mechanism, it is an attractive target for antiviral therapeutics with high target specificity and low host cytotoxicity (10).

The concept of using RNA molecules as therapeutic agents has aroused increasing interest in the past decade. Antisense RNAs and trans-cleaving ribozymes have been studied as potential inhibitors of HCV translation (11, 12). Recently, RNA interference using small interfering RNAs has proved to be highly efficient in inhibiting the replication of a number of viruses including HCV (3).

Another strategy of blocking the replication of RNA viruses has been to express small and structured viral RNA elements in target cells. These RNAs bind to viral regulatory proteins and prevent their binding to corresponding sequences in the viral RNA thus inhibiting viral gene expression. Overexpression of Human Immunodeficiency Virus (HIV) trans-activation response region and Rev response element RNAs in CD4+ T cells prevented the binding of viral Tat and Rev proteins to the viral RNA and made the cells resistant to HIV replication (13, 14). Also, a 60 nt RNA termed IRNA, isolated from *Saccharomyces cerevisae*, has been shown to block IRES-mediated translation of poliovirus and HCV by sequestering cellular trans-acting factors which interact with the viral IRESs (15, 16). La and PTB-specific SELEX RNA have also been shown to inhibit HCV IRES-mediated translation (17, 18).

The limitations of the above-referred known procedures to inhibit the HCV translation/replication is the non-specificity of the procedures and also the possibility of the generation of escape mutants of the virus. Any sequence based approach like RNA interference or antisense has the possibility of generating resistant varieties of the virus because of increased selection pressure. Also, there is a possibility of the function of certain cellular genes being affected.

Herein, a novel approach to inhibit HCV IRES-mediated translation using small RNA molecules mimicking the structure of the defined SL (stem-loop) domains of the HCV IRES is being demonstrated. It has been shown that a small RNA molecule corresponding to domain III of the HCV IRES and a smaller molecule corresponding to the SL III e+f subdomain binds to specific cellular proteins interacting with the HCV IRES and strongly inhibit HCV IRES-mediated translation without inhibiting cap-dependent translation.

Therefore, the specific inhibition of HCV IRES-mediated mechanism by the SL III e+f RNA of the HCV 5'UTR has a potential to be used as a therapeutic strategy with a number of associated advantages. Firstly, as the RNA-protein interactions between host cellular proteins and a highly conserved region of the viral RNA are targeted, the chance of generation of viral escape mutants is very low. Any sequence-specific antiviral molecule would exert a selection pressure for the generation of escape variants. On the other hand, a strategy targeting the interaction between host proteins and the viral RNA would not exert a strong selection pressure on the viral genome as the rate of mutation of cellular proteins is entirely independent of viral replication. Moreover, the activity of the HCV IRES being highly structure dependent, only mutational events which can alter the structure in such a way as to enable it to interact with a different protein with the same function or which increases the affinity to an existing interacting partner would allow the virus to circumvent inhibition mediated by this approach. Secondly, the RNA molecule being a part of the viral genome, if administered prophylactically to patients already harbouring the viral RNA, it is not expected to give rise to non-specific immune responses as seen in the case of antisense RNAs (Dove, 2002). Thirdly, as the inhibitory activity is dependent on the RNA structure, stabler derivatives using different nucleotide (eg. phosphorothioate) or backbone (eg. PNA) chemistries and small molecule structural analogs of the RNA can be utilized to increase the deliverability and stability of the therapeutic molecule.

Accordingly, it is the primary object of the present invention to investigate whether small RNA molecules corresponding to the different stem-loop (SL) domains of the HCV IRES, when introduced in trans, can bind to the cellular proteins and antagonize their binding to the viral IRES, thereby inhibiting HCV IRES-mediated translation.

It is another object of the present invention to identify the RNA molecule corresponding to a sub-domain of SL III region of the HCV IRES, which could efficiently inhibit HCV IRES-mediated translation in a dose-dependent manner without affecting cap-dependent translation.

A further object of the present invention is to provide a small synthetic nucleic acid sequence GGGA GGGC CCTCTCG GTAGA ACACCA TGACGGA CTATCCCAC-GAACGCTCACGGGGCCCTCC (SEQ ID No. 1).

A further object of the present invention is to provide a therapeutic molecule/composition, which will be useful in the treatment of hepatitis C induced liver cirrhosis and hepato cellular carcinoma and a method of preparing the said composition.

Further objects of the present invention are providing a polynucleotide, a recombinant vector, a method of preparing the same using the synthetic HCV IRES ribonucleic acid and a method for inhibiting HCV IRES mediated translation.

SUMMARY OF INVENTION

HCV is a positive stranded RNA virus and the translation of the viral genomic RNA to produce the proteins required for replication is an early obligatory step of the infection process.

The translation initiation of the uncapped viral RNA takes place through the highly structured Internal Ribosome Entry Site (IRES) located in the 5'UTR of the viral RNA. The process of IRES-mediated translation is an attractive target for designing antiviral therapeutics with high target specificity and low host cytotoxicity because of its fundamental difference from the cap-dependent translation of cellular proteins and its importance in the viral life cycle.

The cap independent internal initiation of translation is mediated by the interaction between the cellular trans acting factors with the cis acting elements within the HCV 5'UTR RNA.

The present invention proposes a molecular approach to inhibit HCV IRES-mediated translation by using small RNA molecules analogous to the structure of the defined stem-loop (SL) domains of the HCV 5'UTR (IRES element). These RNA molecules, when introduced in trans, were expected to specifically bind to the cellular proteins that interact with the viral IRES and are required for internal initiation of translation. As a result of this sequestration, the cellular proteins would be prevented from binding to the IRES of the viral RNA and this may lead to the inhibition of viral protein synthesis.

When the above proposal was tested experimentally, it has been observed that a small RNA molecule corresponding to domain III of the HCV IRES and a smaller molecule corresponding to the SL III e+f subdomain binds to specific cellular proteins interacting with the HCV IRES and strongly inhibit HCV IRES-mediated translation without inhibiting cap-dependent translation in vitro and in vivo in cultured cells. Further, the SLIII e+f RNA was found to interact with the 40 S ribosomal subunit protein S5. As the S5 protein of the 40S subunit is crucial for ribosome binding to the HCV IRES, binding of the SL III e+f RNA to the S5 protein blocked the ribosome interaction with the HCV IRES and resulted in the inhibition of translation initiation (Ray and Das, 2004, Nucleic Acids Res).

These observations helped to conclude that a small RNA molecule analogous to a specific stem-loop structure of the HCV IRES can be used to selectively inhibit HCV IRES-mediated translation. Small molecule structural analogs of the SL III e+f RNA, that prevent the binding of ribosomes to the HCV IRES by interacting with the S5 protein, may be developed, which might act as potent inhibitors of HCV translation and may act as novel antivirals to combat HCV infection.

BRIEF DESCRIPTION OF THE ACCOMPANYING DRAWINGS

(A) Proposed secondary structure of the HCV Ires RNA spanning nucleotides 40-372 of the 5'UTR of the viral RNA (SEQ ID No. 2). The domains that were PCR amplified and cloned to generate small RNAs are delineated. (B) 100-fold and 200-fold molar excess of in vitro transcribed SL II, III and IV RNAs were added to in vitro translation reactions of HCV vicistronic RNA. 5.mu.l of the translation reactions was resolved on SDS-12.5% PAGE and exposed for phosphorimaging. The fluc and Rluc protein products are indicated by arrows. (C) The percent Fluc activity representing the efficiency of HCV IRES-mediated translation from a HCV bicistronic template in presence of six increasing concentrations of SL II, III and IV RNAs. The Fluc activity at each concentration is represented as a percentage of the control reaction (expressed as 100%). (D) The percent Rluc activity representing the efficiency of cap-dependent translation from the same set of experiments were plotted. The Rluc activity at each concentration is represented as a percentage of the control reaction. The translation efficiency was not reduced to below 50% by either SL III or SL II.

(A) Three-way co-transfections were performed in HeLa cells using pRL-CMV, pCD-HCV5'UTR-Fluc and two concentrations of pCD-SL III and pCD-SL II DNAs. DNA quantity per dish was normalized by transfecting pGEM-3Z DNA. The black bars represent Fluc activity (HCV IRES-mediated translation) whereas the gray bars represent Rluc activity (cap-dependent translation). (B) The same experiment was repeated in the Huh7 cell line. Combined data from three independent experiments in each cell line are shown. Luciferase activity in control reactions is expressed as 100%. Values which significantly differ from controls (P<0.01) are indicated by asterisks.

(A) Huh7 cells were transfected with an eukiaryotic expression vector encoding the SL III RNA, upstream of a ribozyme sequence (schematically represented), which generated the SL III RNA in vivo. (B) The cells were selected by G418 selection to generate a cell line constitutively expressing the SL III RNA. RT-PCR of total RNA isolated from untransfected Huh7 cells and cells stably transfected with the pCD-SL III-Ribo DNA using SL III-specific or actin-specific primers. The amplified products are indicated. (C) in vivo metabolic labelling of Huh7 and Huh7-SLIII cells using $^{35}$S-MET/$^{35}$S-Cys. The cells were lysed after labelling and the cell lysates resolved by SDS-10% PAGE.

(A) Proposed secondary structure of HCV IRES (internal ribosome entry site) domain III (121-315 nt) (SEQ ID No. 3), delineating the SL structures, which were generated by oligonucleotide-driven transcription. (B) Schematic representation of the process of oligonucleotide-driven transcription of the HCV IRES SL RNAs using synthetic oligonucleotide templates (C) The percent Fluc activity representing the efficiency of HCV IRES-mediated translation from a HCV bicistronic template in presence of five increasing concentrations of SL III a+c, b, d and e+f RNAs was plotted. Luciferase activity in control reactions is expressed as 100%. (D) The percent Rluc activity representing the efficiency of cap-dependent translation from the same set of experiments was plotted. The reporter gene activity at each concentration is represented as a percentage of the control reaction.

Huh 7 cells were co-transfected with 6 µg of in vitro transcribed capped HCV bicistronic RNA and two concentrations (6 and 12 µg) of either SL III e+f RNA or SL III d RNA. The RNA quantities in each dish were normalized by adding appropriate amounts of an in vitro transcribed RNA corresponding to the polylinker sequence of the pGEM 3Z plasmid. The black bars represent Fluc activity whereas the gray bars represent Rluc activity. Luciferase activity in control reactions is expressed as 100%. Values which significantly differ from controls (P<0.01) are indicated by asterisks.

(A) Representation of the SL III e+f RNA (SEQ ID No. 4) showing the mutation of A297 to G (SEQ ID No. 5). (B) $^{32}$P-labeled RNAs corresponding to SL III e+f and SL III e+f (A297G) were UV-crosslinked to HeLa S10 extract and digested with RNase A. The nucleoprotein complexes were resolved by SDS-15% PAGE and the position of p25 is indicated. (C) The same RNAs were UV-crosslinked to purified S5 ribosomal protein and the nucleoprotein complexes were resolved by SDS-15% PAGE. (D) 100-fold and 200-fold molar excess of in vitro transcribed SL III e+f (A297G) RNA was added to in vitro translation reactions of HCV bicistronic RNA and luciferase activity was assayed. The black bars represent Fluc activity (HCV IRES-mediated translation) whereas the gray bars represent Rluc activity (Cap-dependent translation). Luciferase activity in control reactions is expressed as 100%. Combined data from three independent experiments is represented.

(A) Sucrose gradient sedimentation profiles of $^{32}$P-UTP-labeled HCV 5'UTR RNA incubated in RRL in absence and presence of 200 fold excess of unlabeled SL III e+f RNA. (B) Sedimentation profile of radiolabeled HCV 5'UTR RNA in presence of 2 mM GMP-PNP and in the presence or absence of 200 fold excess of unlabeled SL III e+f RNA. The filled circles represents the control reaction profile and the open circles show the profile in the presence of SL III e+f. Both profiles show the counts per minute as a percentage of the total counts added to the reaction (~10$^5$ cpm) against the fraction number of the gradient. The fractions were collected from the bottom upwards. The 80S and 48S ribosomal peaks are indicated.

(A) Sucrose density gradient sedimentation profiles of $^{32}$P-UTP-labeled capped-GFP RNA incubated in RRL in absence and presence of 200 fold excess of unlabeled SL III e+f RNA. (B) Sedimentation profile of radiolabeled HCV 5'UTR-GEP RNA in presence or absence of 200 fold excess of unlabeled SL III e+f RNA. The filled circles represents the control reaction profile and the open circles show the profile in the presence of SL III e+f. (C) Sucrose density gradient sedimentation profile of $^{32}$P-UTP-labeled SL III e+f RNA incubated in RRL. All the profiles show the counts per minute as a percentage of the total counts added to the reaction (~10$^5$ cpm) against the fraction number of the gradient. The fractions were collected from the bottom upwards. The 48S ribosomal peak and the polysomal peaks are indicated.

The HCV IRES binds to the 40S ribosomal subunit as demonstrated by Spahn et al., 2001, making contact with the S5 protein (shaded in red) via SL III e and f and SL II.

When SL III e+f RNA is added in trans, it binds to the S5 protein on the 40S subunit (shown in blue) and blocks this crucial binding site for the HCV IRES RNA. This prevents ribosome recruitment by the HCV IRES and thereby inhibits HCV IRES-mediated translation. The 40S subunit, HCV IRES and SL III e+f RNA representations are not to scale.

PREPARATION OF THE INHIBITOR RNA

Oligonucleotide-Driven Transcription of SLIIIe+f RNA

The inhibitor RNA was synthesized by in vitro transcription assay using standard protocol described earlier (15) and also in the Promega Protocol. Briefly, synthetic DNA oligonucleotides corresponding to domain III stem-loops e+f structures with T7 promoter sequences at the 5' end (GG-GAGGGCCCTCTCGGTAGAACACCAT-GACGGACTATCCCACGAACGCTCA GGGGCCCTCC) was obtained from Sigma Aldrich (St. Louis, Mo.). The oligonucleotide was annealed to T7 RNA polymerase promoter primers and transcribed in vitro using T7 RNA polymerase as described earlier. The transcription reaction was extracted with phenol and chloroform. The synthesized RNA was purified and concentrated by alcohol precipitation. The RNA pellet was dried in vaccum centrifuge and dissolved in nuclease free water.

The SL IIIe+f (A297G) oligo had the same sequence as the SL III e+f oligo except for a T residue replaced by C at the 54$^{th}$ position. Radioactively labeled RNAs were synthesized similarly using the same templates and $\alpha$-$^{32}$P-UTP.

In order to express the inhibitor RNA in vivo from eukaryotic expression vector, the oligonucleotide DNA sequences corresponding to the inhibitor RNA (SLIII e+f) was annealed with the antisense oligonucleotide to make double stranded DNA and then cloned into pCDNA3 vector (Invitrogen). The RNA corresponding to SLIII e+f sequences were generated in vitro by Runoff transcription using T7 RNA polymerase and the RNA was tested for its inhibitory effect in the in vitro translation assays.

Examples of Assay:

In vitro translation: In vitro translation was carried out using 1 µg of template RNA in 17 µl of micrococcal nuclease-treated Rabbit Reticulocyte Lysate (RRL) medium (Promega) and either 0.5 µl each of amino acid mixtures minus methionine and minus cysteine or 20 µCi of $^{35}$S methionine (Perkin Elmer). The reaction mixtures were pre-incubated with in vitro transcribed small RNAs as indicated in the results. After adding template RNA, the reaction mixtures were incubated at 30° C. for 1 h 30 min, and the products were analyzed either by Dual Luciferase assay system (Promega) in a TD 20/20 Luminometer (Turner Designs, Sunnyvale, Calif.) or resolved on SDS-12.5% polyacrylamide gel followed by phosphorimaging (Fuji Imaging, Japan).

DNA and RNA transfection: 60%-70% confluent monolayers of HeLa and Huh 7 cells in 35-mm dishes were co-transfected with plasmid DNAs using Tfx 20 reagent (Promega) as indicated in results. The cells were harvested 48 h after transfection and luciferase activity was assayed. Huh 7 cells were co-transfected with in vitro transcribed RNAs using Tfx 20 reagent as indicated in results. The cells were harvested 16 h after transfection and luciferase activity was assayed. DNA and RNA quantities were normalized using pGEM 3Z DNA (Promega) or an in vitro transcribed RNA corresponding to its polylinker sequence. Huh 7 cells were transfected with the BB7 HCV subgenomic replicon RNA followed by retransfection with SL III e+f RNA after 16 h. 24 h after transfection with SL III e+f, the cells were harvested and the total RNA was isolated using Tri Reagent (Sigma Aldrich).

Ribosomal Assembly assay: $^{32}$P-labeled HCV 5'UTR RNA (~10$^5$ cpm) was added to 25 µl of translation reaction containing 17.5 µl RRL, in presence or absence of 200 fold excess of SL III e+f RNA. 2 mM 5'-Guanylyl-imidophosphate (GMP-PNP, Sigma Aldrich) was added to the reaction as indicated in the results. The reactions were incubated at 30° C. for 15 min, diluted to 150 µl with gradient buffer (20 mM Tris-Cl, pH 7.5, 100 mM KCl, 3 mM MgCl$_2$, 1 mM DTT) and overlaid on a 5%-30% linear sucrose gradient. The ribosomal complexes were sedimented by ultracentrifugation for 3 h at 4° C. and 30000 rpm. 500 μl fractions were collected from the bottom of the column and the radioactivity was measured in a liquid scintillation counter.

Methodology for Other Experiments and Data Analysis:

in vitro transcription: The plasmid pRL-HCV1b was linearized downstream of Fluc and transcribed using T7 RNA polymerase in the presence of RNA Cap Analog (Invitrogen) to generate the bicistronic capped RNA. The plasmids pCD-SL II, SLIII and SL IV were linearized with Eco RI and transcribed by in vitro run-off transcription reactions under standard conditions using reagents from Promega. $^{32}$P-labeled HCV 5' UTR RNA and the SL RNAs were transcribed from respective plasmids using T7 RNA polymerase and α-$^{32}$p Uridine tri-phosphate (Perkin Elmer Life Sciences, Boston, Mass.).

Ultraviolet light-induced crosslinking of proteins with RNA: The in vitro transcribed $^{32}$P-labeled RNAs were incubated with HeLa S10 extract or purified protein in 2×RNA binding buffer and UV-crosslinked as described earlier (19). Unbound RNAs were digested by treatment with 30 μg of RNase A at 37° C. for 30 min. The protein-nucleotidyl complexes were electrophoresed on SDS-10% polyacrylamide gels followed by autoradiography.

Statistical analysis: The mean±SD of five independent in vitro translation experiments is represented. Data from the co-transfection experiments is expressed as mean±SD of three independent replicates. The significance of differences between means was tested by Student's t test. IC$_{50}$ values for inhibitory RNAs were determined by non-linear regression analysis of the inhibition curves using SigmaPlot (SPSS Inc., Chicago, Ill.).

Experimental Evidences:

1. Specific inhibition of HCV IRES-mediated translation by RNA corresponding to SL III of the HCV 5'UTR.

Figure 1:
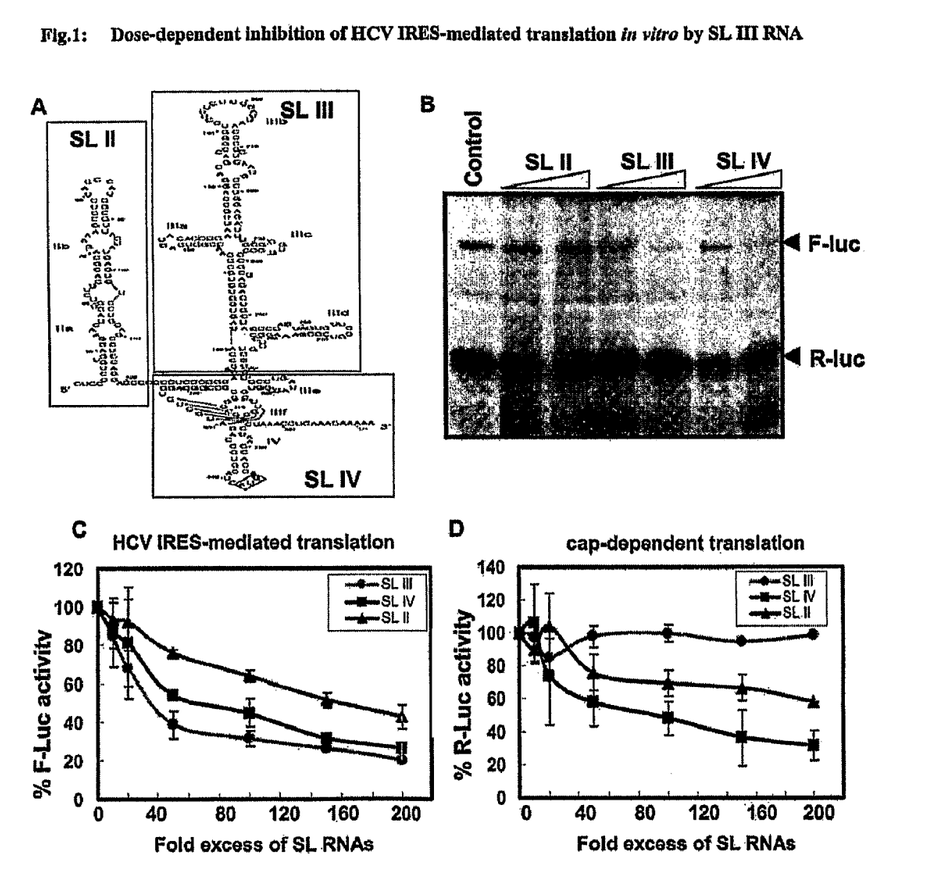
FIG. 1: Dose-dependent inhibition of HCV IRES-mediated translation in vitro by SL III RNA.

RNAs corresponding to the three major domains of the HCV 5'UTR: SL II, SL III (excluding SL III e+f) and SL IV (including SL III e+f) (FIG. 1A) were transcribed in vitro. 100-fold and 200-fold excess of these RNAs was exogenously added to in vitro translation reactions of the Rluc-HCV-Fluc bicistronic RNA and the reporter gene products were radiolabeled (FIG. 1B). The three RNA molecules differentially inhibited HCV IRES-mediated translation of Fluc and cap-dependent translation of Rluc in a dose-dependent manner. SL II did not significantly inhibit either IRES-mediated or cap-dependent translation whereas SL IV was found to inhibit both. SL III RNA was found to strongly inhibit HCV IRES-mediated translation with no significant effect on cap-dependent translation (FIG. 1B). Similar results were obtained when the luciferase activity from non-radiolabeled reporter gene products was assayed (FIG. 1C). SL III RNA caused a maximum 80% reduction of Fluc activity whereas there was 73% and 57% inhibition at corresponding doses of SL IV and SL II respectively (FIG. 1C). IC$_{50}$ values for SL III, IV and II were determined to be respectively 35-fold, 60-fold and 152-fold excess of the template RNA. There was no significant inhibition of Rluc activity by either SL III or SL II, whereas SL IV caused 68% inhibition at 200-fold excess concentration (FIG. 1D). These observations indicate both an efficient and selective inhibition of HCV IRES-mediated translation by SL III which was significantly higher than that caused by SL II or SL IV RNA (P<0.01). SL IV caused a strong inhibition of both HCV IRES-mediated translation and cap-dependent translation whereas the effect of SL II on either was not pronounced.

2. Specific inhibition of HCV IRES-mediated translation in vivo.

Figure 2:
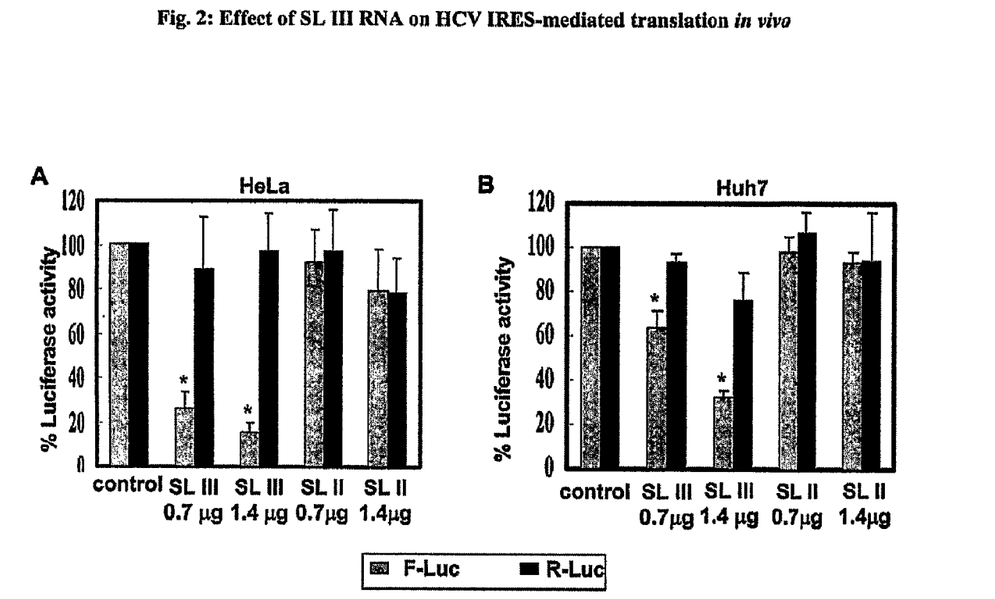
FIG. 2: Effect of SL III RNA on HCV IRES-mediated translation in vivo.

As SL III was found to strongly inhibit HCV IRES-mediated translation in vitro, we next tested its translation inhibitory activity in vivo. For this purpose, three-way co-transfections were performed in HeLa and Huh7 cells using pRL-CMV, pCD-HCV-Fluc and two different concentrations of pCD-SL III and pCD-SL II DNAs. The pCD-HCV-Fluc contained the entire 341 nt long HCV 5'UTR together with 42 nt from the coding region of the core to maintain the pseudoknot structure around SL IV and enhance the efficiency of translation. pRL-CMV was used to generate a capped Rluc transcript in vivo. Approximately 100 ng of both the plasmid DNAs were co-transfected along with two concentrations of either SL II or SL III encoding DNA. SL II, which had not shown a significant effect on either IRES-mediated or cap-dependent translation in vitro, was utilized as the negative control in these experiments. The combined data obtained from three co-transfection experiments in HeLa cells showed that SL III significantly (P<0.01) inhibited the HCV IRES-driven translation of Fluc at both concentrations (74% and 85% inhibition respectively) whereas there was no significant effect on the cap-dependent translation of Rluc (FIG. 2A). The effect of SL II on both cap-dependent and IRES-mediated translation in vivo was not significant compared to the control. The co-transfection experiments were repeated in Huh7 cells which is a human hepatocellular carcinoma cell line supporting efficient HCV replication. There was a significant inhibition (P<0.01) of HCV IRES-mediated translation by SL III (FIG. 2B) although the extent of inhibition was comparatively less (37% and 68% inhibition at two concentrations) than that observed in HeLa cells using similar quantities of transfected DNA. These data demonstrate that SL III RNA could specifically inhibit HCV IRES-mediated translation in both non-liver-derived (HeLa) and liver-derived (Huh7) cells.

3. Specific inhibition of HCV IRES-mediated translation in vivo in hepatocellular carcinoma cells constitutively expressing the inhibitor SLIII RNA.

In order to investigate whether the constitutive expression of the SL III RNA in cells had any cytotoxic effect, a Huh7 cell line, stably transfected with the pCD-SL III-Ribo plasmid (FIG. 3A), was generated.

Figure 3:
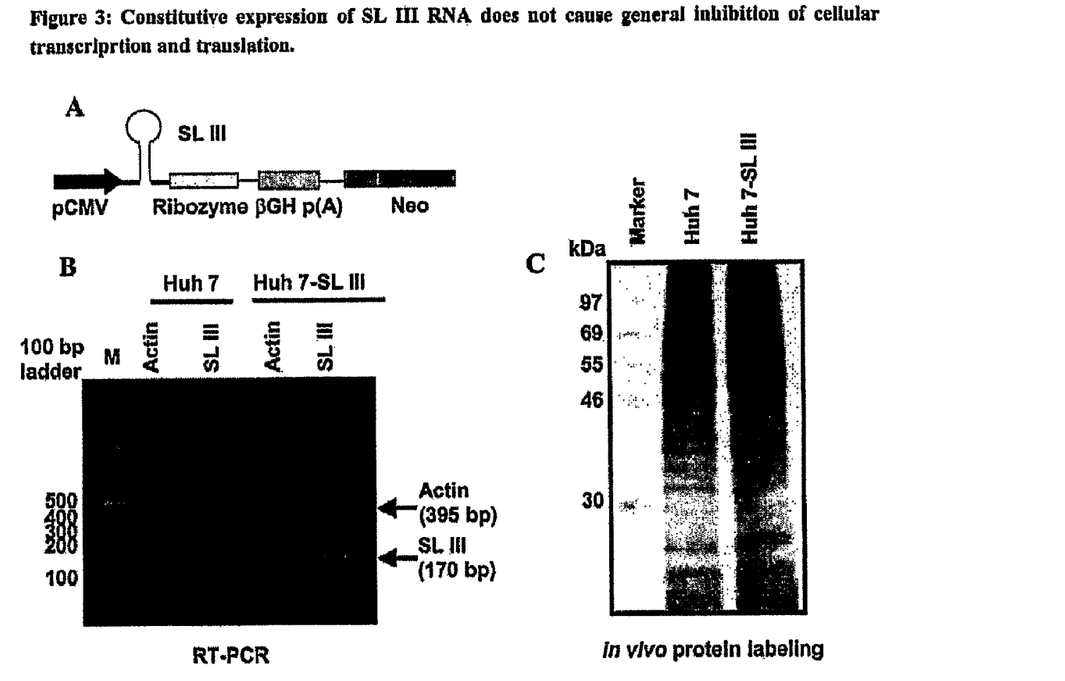
FIG. 3: Constitutive expression of SL III RNA does not cause general inhibition of cellular transcription and translation.

This cell line, Huh-HCVSLIII did not show any cytotoxic effect for the period of four months during which it was monitored. Other parameters like cellular morphology and doubling time also remained unchanged. The constitutive expression of the SL III RNA was investigated by RT-PCR analysis of total RNA extracted from these cells using SL III specific primers. Semi-quantitative RT-PCR showed that the SL III RNA was expressed at a high level in the Huh-HCVS-LIII cell line, but was absent in untransfected Huh7 cells (FIG. 3 B). A control RT-PCR using β-actin specific primers demonstrated that the level of transcription of actin in the Huh-HCVSLIII cells was similar to that in untransfected Huh7 cells, suggesting that the transcription of a housekeeping gene like actin was not compromised in these cells (FIG. 3 B).

In order to investigate the effect of SL III expression on cellular protein synthesis, Huh-HCVSLIII cells and untransfected Huh7 cells were metabolically labeled using $^{35}$S-Met/$^{35}$S-Cys and the proteins were resolved by SDS-PAGE. No difference in the cellular protein synthesis between the stably transfected and untransfected cells was observed (FIG. 3C).

When the Huh-HCVSLIII cells were transfected with a HCV bicistronic plasmid, HCV IRES-mediated translation was found to be significantly reduced. However, cap-dependent translation was also reduced, specially when low amounts of the bicistronic DNA were transfected, suggesting that constitutive over-expression of the SL III RNA could inhibit cap-dependent translation to some extent, possibly by sequestering some of the protein factors required for cap-dependent translation initiation.

4. Inhibition of HCV IRES-mediated translation by an RNA corresponding to SL III e+f.

Figure 4:
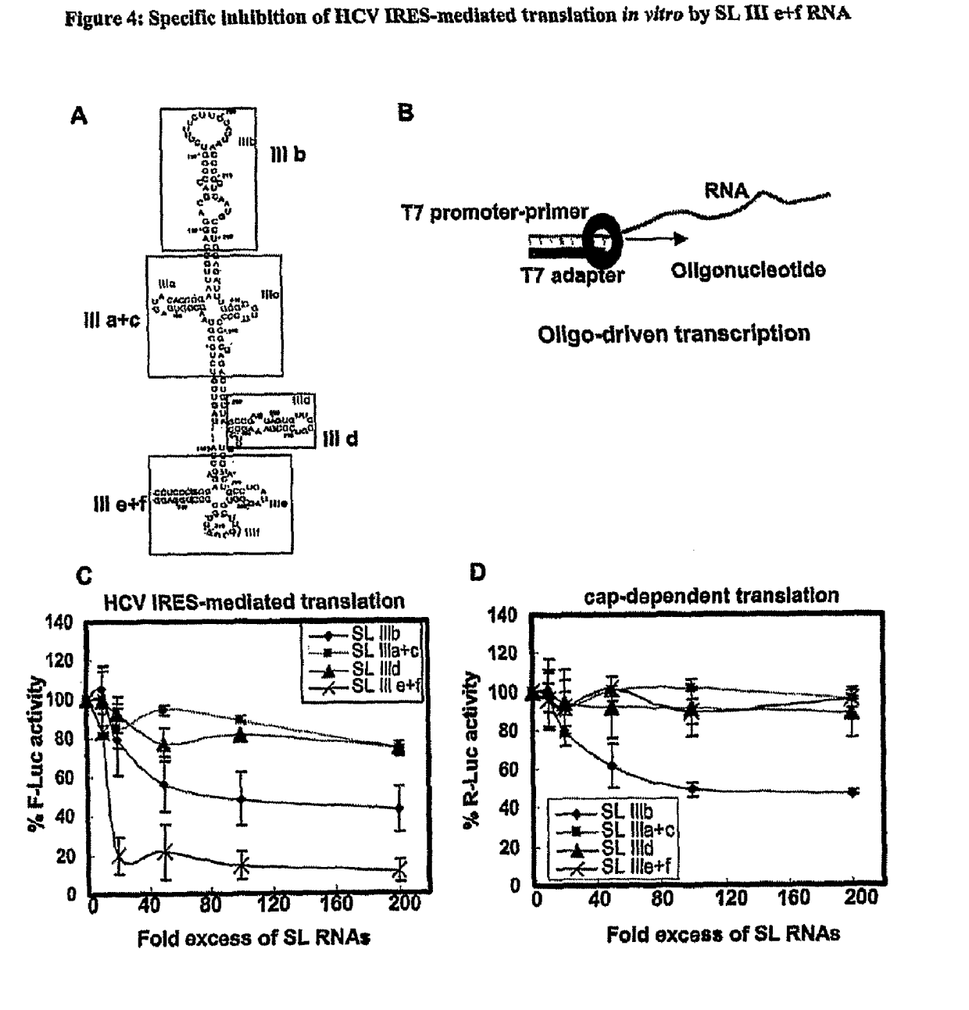
FIG. 4: Specific inhibition of HCV IRES-mediated translation in vitro by SL III e+f RNA.

As RNA molecules corresponding to domain III of the HCV IRES showed the maximum translation inhibitory effect, we tried to generate smaller RNAs corresponding to its specific subdomains that could inhibit HCV IRES-mediated translation. Increasing concentrations of small RNAs corresponding to the SL III a+c, b, d and e+f subdomains (FIG. 4A) were exogenously added to in vitro translation reactions of the HCV bicistronic RNA. The RNAs were synthesized by oligonucleotide-driven transcription, as described schematically in FIG. 4B. Interestingly, SL III e+f RNA caused a very strong inhibition (89% reduction from control) of HCV IRES mediated translation (FIG. 4C) with no significant effect on cap-dependent translation (FIG. 4D). SL III b caused 57% inhibition of HCV IRES-mediated translation but this was accompanied by a 53% decrease in cap-dependent translation (FIGS. 4C and D). SL III a+c and III d RNAs showed minor reductions in the efficiency of HCV IRES-mediated translation. The $IC_{50}$ of SL III e+f RNA was calculated to be 15-fold excess of template RNA. These observations demonstrated that the small RNA corresponding to SL III e+f subdomain could strongly inhibit HCV IRES-mediated translation in vitro without significantly inhibiting cap-dependent translation.

5. Effect of SL m e+f RNA on HCV IRES-mediated translation in vivo.

Figure 5:
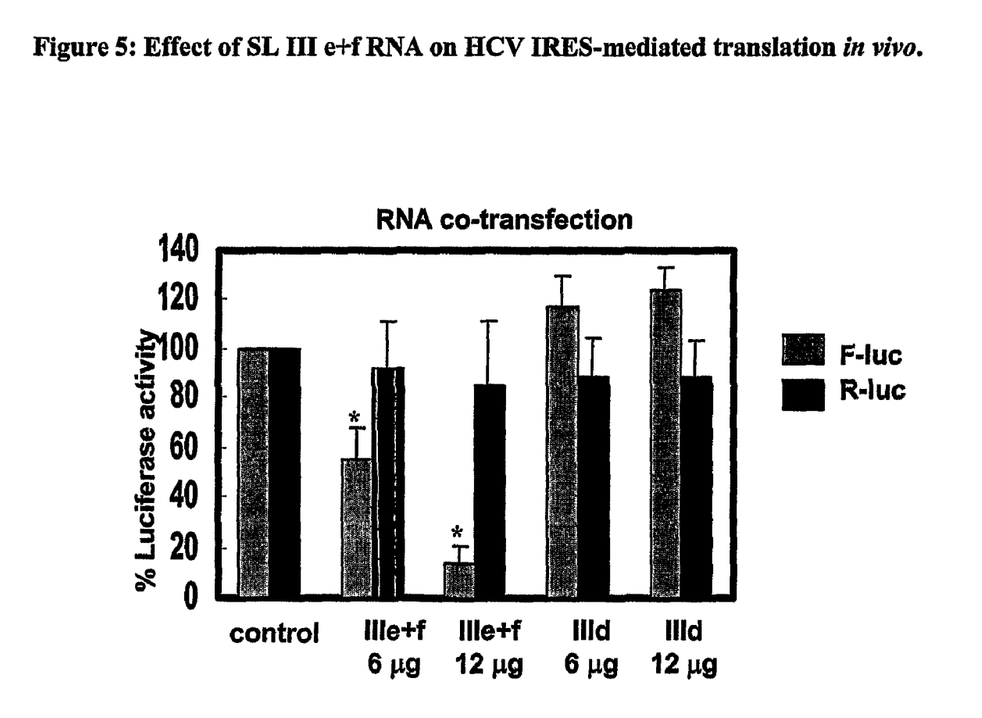
FIG. 5: Effect of SL III e+f RNA on HCV IRES-mediated translation and replication in vivo.

As SL III e+f RNA showed a strong inhibition of HCV IRES-mediated translation in vitro, we next investigated its effect on HCV translation in vivo. Huh 7 cells were co-transfected with in vitro transcribed HCV bicistronic RNA together with two concentrations of SL III e+f RNA. SL III d, which had not shown a significant effect, was used as the negative control. SL III e+f RNA significantly inhibited (P<0.01) HCV IRES-mediated translation in a dose dependent manner (45% and 85% inhibition at the two concentrations) with no significant inhibition of cap-dependent translation. Addition of SL III d RNA did not cause any inhibition of either IRES-mediated or cap-dependent translation (FIG. 5).

Figure 6:
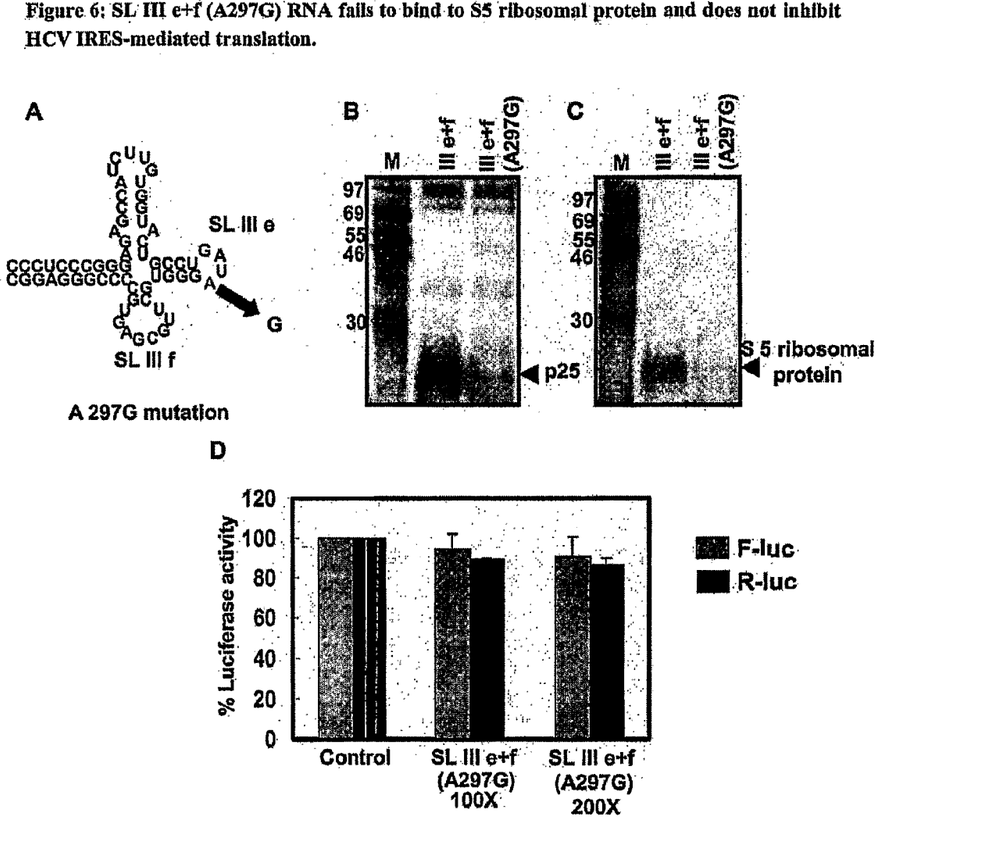
FIG. 6: SL III e+f (A297G) RNA fails to bind to S5 ribosomal protein and does not inhibit HCV IRES-mediated translation.

As SL III e+f RNA was found to strongly inhibit HCV IRES-mediated translation in vitro and in vivo, we investigated the protein binding profile of the RNA to correlate it with the translation inhibitory activity. The SL III subdomain RNAs demonstrated differential binding to specific proteins that interacted with the HCV domain III RNA (FIG. 6A). A 25 kDa protein was found to interact strongly with SL III e+f RNA but did interact with the other RNAs. This protein may correspond to the S5 ribosomal protein as a single mutation in this region of the HCV 5'UTR has been shown to abrogate the binding of this protein (19). In order to investigate this possibility, bacterially expressed S5 ribosomal protein was used for UV-crosslinking assay. SL III e+f RNA strongly interacted with the purified protein whereas SL III d, which had not shown any interaction with p25 from HeLa cells, failed to do so (FIG. 6B). The full length HCV 5/'UTR also interacted with the S5 protein, but to a lesser extent than SL III e+f. Therefore, the small RNAs corresponding to the subdomains of domain III could bind to a number of cellular proteins which interacted with the HCV IRES and SL III e+f uniquely interacted with the S5 ribosomal protein.

6. Effect of point mutation within SLIII e+f sub-domain.

As SL III e+f RNA was found to strongly inhibit HCV IRES-mediated translation in vitro and in vivo, and was also found to interact with the S5 ribosomal protein, we investigated whether the binding to the S5 protein was specific and was responsible for its inhibitory activity. A single mutation in SL III e (A297G) of the HCV 5' UTR has been shown to abrogate the binding of the S5 protein to the full-length HCV IRES RNA. An in vitro transcribed mutant SL III e+f RNA, harbouring the A297G mutation in SL III e (FIG. 6A), showed a drastic reduction in binding to the p25 protein from HeLa cytoplasmic extract and also the purified S5 protein (FIGS. 6B and 6C). 100 and 200 fold molar excess of this mutant SL III e+f RNA also failed to inhibit HCV IRES-mediated translation in vitro (FIG. 6D). These observations suggested that the SL III e+f RNA inhibited HCV IRES-mediated translation specifically by binding to the S5 ribosomal protein.

7. SL III e+f RNA prevented the assembly of ribosomal complexes on the HCV IRES.

Figure 7:
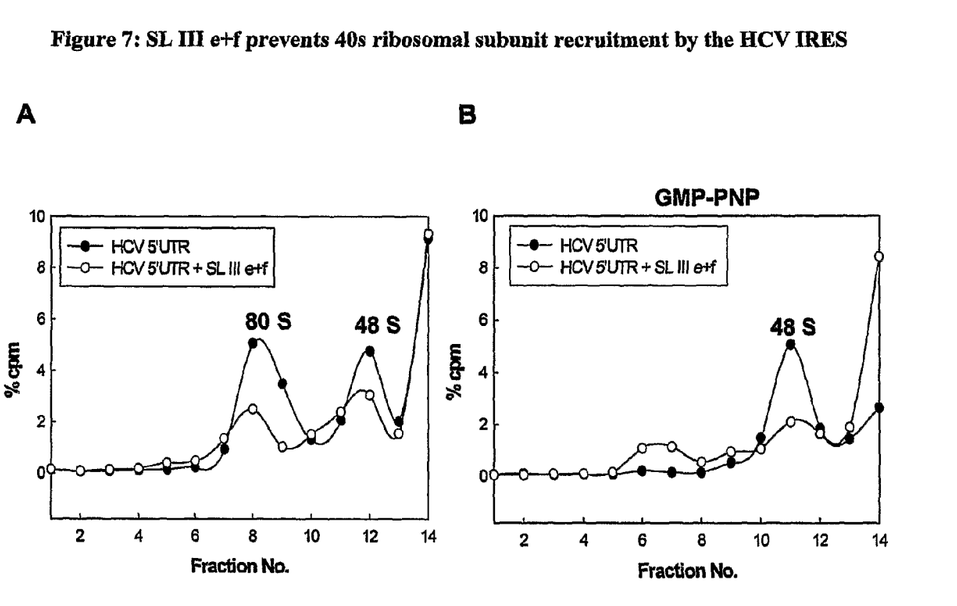
FIG. 7: SL III e+f prevents 40S ribosomal subunit recruitment by the HCV IRES.

The binding of the 25 kDa S5 ribosomal protein has been suggested to be crucial for efficient translation mediated by the HCV IRES (20). As SL III e+f RNA was found to interact strongly with the S5 protein, we investigated its effect on ribosome recruitment by the HCV IRES. For this purpose, ribosomal assembly reactions containing radiolabeled HCV 5'UTR were incubated with 200 fold excess of SL III e+f RNA and analyzed by sucrose density gradient ultracentrifugation. In absence of SL III e+f RNA, HCV IRES showed the formation of both 48S and 80S ribosomal complexes (FIG. 7A, solid line). However, in the presence of SL III e+f RNA, formation of both these complexes was significantly reduced (FIG. 7A, dotted line), suggesting that SL III e+f prevented the assembly of ribosomal complexes on the HCV IRES. For further elucidating the role of SL III e+f RNA, the ribosomal assembly reactions were incubated with GMP-PNP which inhibits translation initiation at the 48S stage by preventing the release of eIF2. Addition of GMP-PNP abolished the 80S peak in the control reaction demonstrating that only the 48S complex was being assembled (FIG. 7B, solid line). In presence of SL III e+f the 48S complex formation was also abrogated suggesting that SL III e+f prevented the binding of the 40S ribosomal subunit to the HCV IRES (FIG. 7B, dotted line). This supported the earlier observation that SL III e+f interacted with the S5 ribosomal protein, a component of the 40S subunit. Taken together, these observations suggest that the SL III e+f RNA inhibited HCV IRES-mediated translation by interacting with a component of the 40S subunit and thereby prevented the ribosomal assembly on the HCV IRES.

Figure 8:
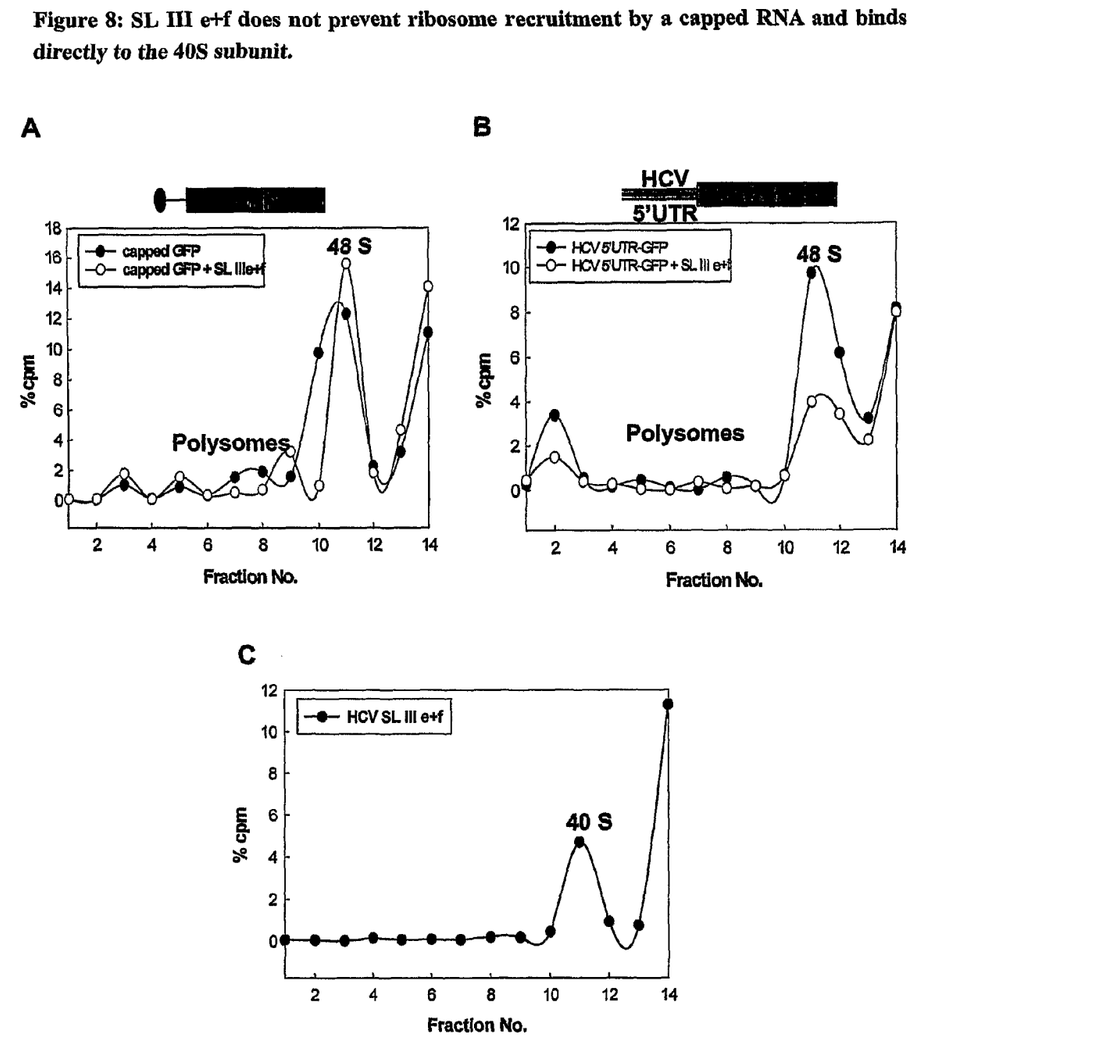
FIG. 8: SL III e+f does not prevent ribosome recruitment by a capped RNA and binds directly to the 40S subunit.

To investigate the effect of SL III e+f RNA on ribosome recruitment by a capped transcript, the ribosome assembly experiment was performed using a radiolabeled capped GFP RNA and 200 fold molar excess of the SL III e+f RNA. As the capped transcript incorporated the protein-coding region of GFP, on sucrose density gradient ultracentrifugation a single 48S peak and a number of smaller peaks corresponding to polysomes was observed (FIG. 8A). 200-fold excess of SL III e+f RNA did not inhibit the formation of either the 48S complex or the polysomes (FIG. 8A). On the other hand, when a radiolabeled transcript containing the GFP gene downstream of the HCV IRES was used for the ribosome assembly reactions 200 fold excess of SL III e+f RNA inhibited the formation of both the 48S complex and the polysome peaks (FIG. 8B). This suggested that SL III e+f specifically abrogated ribosome binding to the HCV IRES and not to capped mRNAs and supported the earlier observation that SL III e+f RNA did not inhibit cap-dependent translation. Finally, as SL III e+f was found to interact with the S5 protein, which is a component of the 40S ribosomal subunit and inhibit ribosome recruitment by the HCV IRES, it was hypothesized that the SL III e+f RNA directly interacted with the 40S subunit. In order to investigate this, ribosome assembly experiments were performed with a radiolabeled SL III e+f RNA. On sucrose density gradient resolution, a single peak corresponding to the 40S subunit bound to the radiolabeled RNA was obtained (FIG. 8C). This suggested that the SL III e+f RNA was able to directly interact with the ribosomal 40S subunit probably via the S5 protein, which is a component of the 40S subunit.

Figure 9:
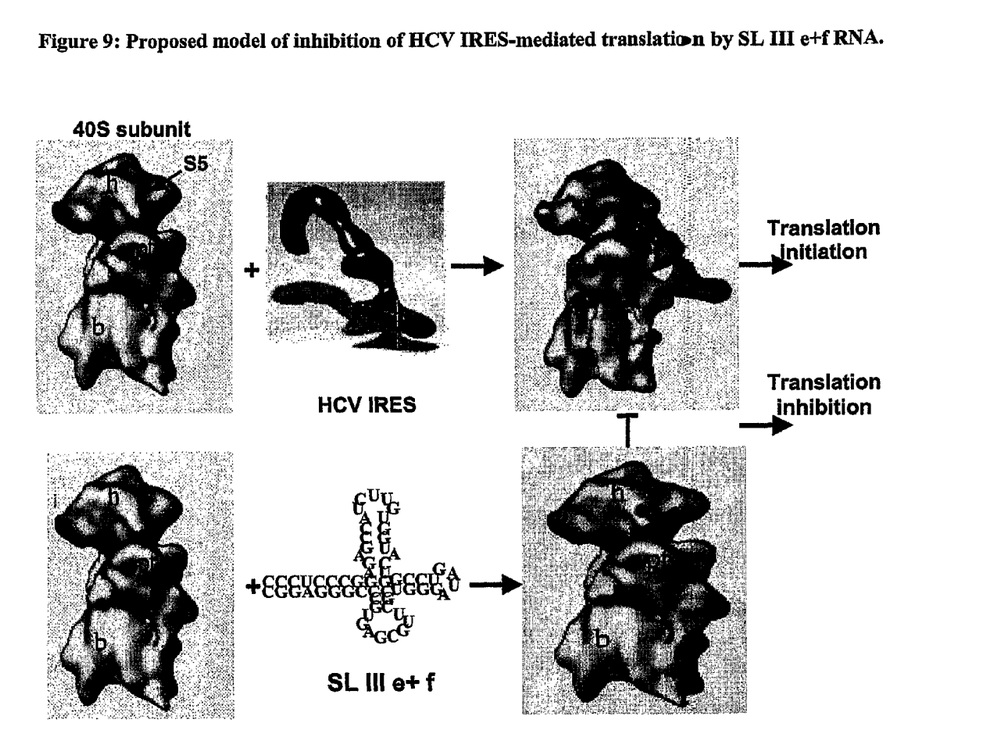
FIG. 9: Proposed model of inhibition of HCV IRES-mediated translation by SL III e+f RNA.

Taken together, these observations indicate that the SL III e+f RNA inhibited HCV IRES-mediated translation by interacting with a component of the 40S ribosomal subunit and thereby preventing the ribosome recruitment by the HCV IRES (FIG. 9, HCV inhibition-model of the present invention).

REFERENCES

1. Jenny-Avital E R. Hepatitis C. Curr Opin Infect Dis 1998; 11:293-299.
2. Lindsay K L. Therapy of hepatitis C: overview. Hepatology 1997; 26:715-755.
3. Randall G, Grakoui A, Rice C M. Clearance of replicating hepatitis C virus replicon RNAs in cell culture by small interfering RNAs. Proc Natl Acad Sci USA 2003; 100: 235-240.
4. Tsukiyama-Kohara K, Iizuka N, Kohara M, Nomoto A. Internal ribosome entry site within hepatitis C virus RNA. J Virol. 1992; 66: 1476-1483.
5. Pudi R, Abhiman S, Srinivasan N, Das S. Hepatitis C virus internal ribosome entry site-mediated translation is stimulated by specific interaction of independent regions of human La autoantigen. J Biol Chem 2003; 278: 12231-12240.
6. Ali N, Siddiqui A. Interaction of polypyrimidine tract-binding protein with the 5' noncoding region of the hepatitis C virus RNA genome and its functional requirement in internal initiation of translation. J Virol 1995; 69: 6367-6375.
7. Sizova D V, Kolupaeva V G, Pestova T V, Shatsky I N, Hellen C U T. Specific interaction of eukaryotic translation initiation factor 3 with the 5' nontranslated regions of hepatitis C virus and classical swine fever virus RNAs. J Virol 1998; 72: 4775-4782.
8. Kruger M, Beger C, Li Q X, Welch P J, Tritz R, Leavitt M, Barber J R, et al. Identification of eIF2Bγ and eIF2γ as cofactors of hepatitis C virus internal ribosome entry site-mediated translation using a functional genomics approach. Proc Natl Acad Sci USA 2000; 97: 8566-8571.
9. Kieft J S, Zhou K, Jubin R, Murray M G, Lau J Y N, Doudna J A. The hepatitis C virus internal ribosome entry site adopts an ion-dependent tertiary fold. J Mol Biol 1999; 292: 513-529.
10. Loft W B, Takyar S S, Tuppen J, Crawford D H G, Harrison M, Sloots T P, Gowans E J. Vitamin B12 and hepatitis C: Molecular biology and human pathology. Proc Natl Acad Sci USA 2001; 98:4916-4921.
11. Wu C H, Wu G Y. Targeted inhibition of hepatitis C virus-directed gene expression in human hepatoma cell lines. Gastroenterology 1998; 114:1304-1312.
12. Welch P J, Tritz R, Yei S, Leavitt M, Yu M, Barber J. A potential therapeutic application of hairpin ribozymes: in vitro and in vivo studies of gene therapy for hepatitis C virus infection. Gene Ther 1996; 3:994-1001.
13. Lee, T C, Sullenger B A, Gallardo H F, Ungers G E, Gilboa E. Overexpression of RRE-derived sequences inhibits HIV-1 replication in CEM cells. New Biol 1992; 4:66-74.
14. Sullenger B A, Gallardo H F, Ungers G E, Gilboa E. Overexpression of TAR sequences renders cells resistant to Human Immunodeficiency Virus replication. Cell 1990; 63: 601-608.
15. Das S, Kenan D J, Bocskai D, Keene J D, Dasgupta A. Sequences within a small yeast RNA required for inhibition of internal initiation of translation: interaction with La and other cellular proteins influences its inhibitory activity. J Virol 1996; 70:1624-1632.
16. Das S, Ott M, Yamane A, Tsai W, Gromeier M, Lahser F, Gupta S, et al. A small yeast RNA blocks hepatitis C virus internal ribosome entry site (HCV IRES)-mediated translation and inhibits replication of a chimeric poliovirus under translational control of the HCV IRES element. J Virol. 1998; 72:5638-5647.
17. Ali N, Pruijn G J M, Kenan D J, Keene J D, Siddiqui A. Human La antigen is required for the hepatitis C virus internal ribosome entry site-mediated translation. J Biol Chem 2000; 275: 27531-27540.
18. Anwar A, Ali N, Tanveer R, Siddiqui A. Demonstration of functional requirement of polypyrimidine tract-binding protein by SELEX RNA during hepatitis C virus internal ribosome entry site-mediated translation initiation. J Biol Chem 2000; 275:34231-34235.
19. Odreman-Macchioli, F., Baralle, F. E. and Buratti, E. (2001) Mutational analysis of the different bulge regions of hepatitis C virus Domain II and their influence on internal ribosome entry site translational ability. *J Biol. Chem.* 276, 41648-41655.
20. Fukushi, S., Kurihara, C., Ishiyama, N., Hoshino, F. B., Oya, A. and Katayama K. (1997) The sequence element of the internal ribosome entry site and a 25-kilodalton cellular protein contribute to efficient internal initiation of translation of hepatitis C virus RNA. *J Virol.*, 71, 1662-1666.
21. Gosert, R. and Moradpour, D. (2002) A new twist to translation initiation of the hepatitis C virus. *Hepatology*, 35, 724-726.
22. Gitlin, L., Karelsky, S and Andino, R. (2002) Short interfering RNA confers intracellular antiviral immunity in human cells. *Nature*, 418, 430-434.
23. Dove A. (2002) Antisense and sensibility. *Nat. Biotechnol.*, 20, 121-124.

The invention claimed is:

1. A synthetic HCV IRES nucleic acid molecule having the sequence of SEQ ID NO. 1.

2. A synthetic HCV IRES ribonucleic acid molecule having the sequence of SEQ ID NO. 4.

3. A polynucleotide comprising the nucleic acid molecule of claim 1.

4. A recombinant vector comprising the polynucleotide of claim 3.

5. A method of synthesizing the ribonucleic acid molecule of claim 2 by an in vitro transcription method.

6. A method for preparing a purified ribonucleic acid (RNA) molecule, comprising the steps of:
  (a) allowing the polynucleotide of claim 3 with T7 promoter sequences at its 5' end, to anneal to T7 RNA polymerase promoter primers and to be transcribed in vitro by T7 RNA polymerase in an in vitro transcription reaction to form an RNA molecule, and
  (b) separating said RNA molecule from the transcription reaction to obtain the purified ribonucleic acid molecule.

7. A method for making a recombinant vector comprising the step of inserting the polynucleotide of claim 3 into a vector.

8. An antiviral composition comprising the ribonucleic acid molecule of claim 2 optionally admixed with a pharmaceutically acceptable carrier, diluent, excipient or adjuvant.

9. A method of manufacturing an antiviral composition for treating liver cirrhosis or hepatocellular carcinoma caused by hepatitis C virus, said method comprising admixing the ribonucleic acid molecule of claim 2 with a pharmaceutically acceptable carrier, diluent, excipient or adjuvant.

10. An HCV IRES ribonucleic acid molecule comprising a fragment consisting of the sequence of SEQ ID No. 5.

11. A method for inhibiting HCV IRES mediated translation, said method comprising the steps of:
  (a) introducing into a person an agent capable of binding to the ribosomal protein S5; and
  (b) allowing said agent to reduce the binding of the 40S ribosomal subunit to the HCV IRES, thereby inhibiting HCV IRES mediated translation
wherein said agent is a molecule selected from the group consisting of polynucleotide having the sequence of SEQ ID No. 1 and polynucleotide having the sequence of SEQ ID No. 4.

12. A synthetic nucleic acid molecule consisting essentially of the sequence of SEQ ID NO. 1.

13. A synthetic ribonucleic acid molecule consisting essentially of the sequence of SEQ ID NO. 4.

* * * * *